United States Patent [19]

Franz et al.

[11] Patent Number: 5,797,873
[45] Date of Patent: Aug. 25, 1998

US005797873A

[54] PROCESS FOR THE PREPARATION OF BONE CEMENTS COMPRISING ACTIVE COMPOUNDS

[75] Inventors: Hans-Werner Franz, Dieburg; Berthold Nies, Fränkisch-Crumbach, both of Germany

[73] Assignee: Merck Patent Gesellschaft mit beschrankter Haftung, Germany

[21] Appl. No.: 967,789

[22] Filed: Nov. 10, 1997

Related U.S. Application Data

[63] Continuation of Ser. No. 528,520, Sep. 15, 1995, abandoned.

[30] Foreign Application Priority Data

Sep. 17, 1994 [DE] Germany ............... 44 33 201.7

[51] Int. Cl.$^6$ ............... A61F 2/28; A61M 31/00
[52] U.S. Cl. ............... 604/49; 623/16; 623/66; 623/901
[58] Field of Search ............... 623/16, 66, 901; 433/180; 604/49

[56] References Cited

U.S. PATENT DOCUMENTS

| | | | |
|---|---|---|---|
| 4,554,686 | 11/1985 | Baker | 623/10 |
| 4,722,948 | 2/1988 | Sanderson | 523/115 |
| 4,797,282 | 1/1989 | Wahlig et al. | 424/422 |
| 5,215,459 | 6/1993 | Ney et al. | 433/215 |
| 5,374,427 | 12/1994 | Stille et al. | 424/423 |

FOREIGN PATENT DOCUMENTS

| | | |
|---|---|---|
| 0 202 445 | 11/1986 | European Pat. Off. |
| 0202445 | 11/1986 | European Pat. Off. |
| 0 301 759 | 2/1989 | European Pat. Off. |
| 20 22 117 | 11/1971 | Germany. |
| 207 655 | 3/1982 | Germany. |
| 1349259 | 4/1974 | United Kingdom. |

OTHER PUBLICATIONS

Langendorff et al., "Cytostaticahaltiger Knochenzement: Neue Aspekte in der Behandlung maligner Knochentumoren", *Langenbecks Arch Chir* (1973) 371:123–136.

*Primary Examiner*—Paul B. Prebilic
*Attorney, Agent, or Firm*—Millen, White, Zelano & Branigan, P.C.

[57] ABSTRACT

The invention relates to a process for the preparation of bone cements comprising active compounds and bone replacement materials or implantable drug depots produced therefrom. The bone cement is composed of a solid component and a liquid component. The active compound is dissolved in an organic solvent, the content of which does not exceed 50% by weight, based on the liquid component, and this solution is mixed with the liquid component or with the solid component.

6 Claims, No Drawings

PROCESS FOR THE PREPARATION OF BONE CEMENTS COMPRISING ACTIVE COMPOUNDS

This application is a continuation of application Ser. No. 08/528,520 filed Sep. 15, 1995 and now abandoned.

BACKGROUND OF THE INVENTION

The invention relates to a process for the preparation of bone cements comprising active compounds and bone replacement materials or implantable drug depots produced therefrom.

Bone cements, bone replacement materials and implantable drug depots based on acrylate plastics have been known for a long time. Polymer materials based on acrylic and/or methacrylic acid esters have proved themselves here on the basis of their biocompatibility, their excellent strength properties, their favorable properties in respect of release of embedded pharmaceutical active compounds and, last but not least, on the basis of their processibility being appropriate for the use.

The usual bone cements are composed of about 50 to 75% by weight of a solid component which comprises a finely divided polymer of acrylic and/or methacrylic acid esters and if appropriate other additives, such as polymerization catalysts, X-ray contrast media, fillers and dyestuffs, and about 25 to 50% by weight of a liquid component which comprises an acrylic and/or methacrylic acid ester monomer and if appropriate other additives, such as polymerization accelerators and stabilizers. For use, the solid component and liquid component are mixed to form a liquid to semi-solid paste and this is brought into a desired shape, if appropriate, or applied at the implantation site for cementing in a prosthesis. The composition hardens by the polymerization reaction induced with the mixing of the components.

For example, a bone cement which, in a normal pack, comprises 2 bags of about 40 g of polymer powder each and 2 ampoules of 20 ml of monomer liquid each is very common. The powder is a fine bead polymer of methyl methacrylate with a copolymer content of methyl acrylate. About 0.5% of dibenzoyl peroxide is added to the powder as a catalyst. Small amounts of chlorophyll are also copolymerized during preparation for characterization of the material. The powder additionally comprises a customary X-ray contrast medium, such as, for example, zirconium dioxide. The associated liquid comprises monomeric methyl methacrylate, to which about 0.7% of dimethyl-p-toluidine is added as a polymerization accelerator and small amounts of hydroquinone are added as a stabilizer. This liquid is also as a rule colored with a small amount of chlorophyll for identification. The powder packaged in polyethylene bags is sterilized with ethylene oxide. The liquid is subjected to sterile filtration and transferred to glass ampoules.

When 2 parts by weight of powder are mixed together with one part by weight of liquid, the dibenzoyl peroxide reacts with the dimethyl-p-toluidine in the liquid, which prompts the free radical polymerization. The mixture is tailored such that it can be used as a dough-like paste after only about one minute. This paste remains kneadable for several minutes and then starts to harden with evolution of heat. After about 5 to 10 minutes, the polymerization has essentially ended. During the polymerization phase, as long as the paste is still deformable, it can be brought into any desired shape, that is to say, for example, can be introduced directly into the body for filling bone cavities or for cementing in prostheses or can be used for the production of shaped articles which harden outside the body and can then be used at any desired points in the body.

For numerous indications, it is desirable for the bone cement to comprise pharmaceutical active compounds. Thus, bone cements comprising cytostatics can be employed for restoring bone defects following removal of bone tumours. Bone cements which comprise antibiotics, antiseptics and, if appropriate, bone growth-promoting substances are advantageous for cementing in prostheses and for osteosynthesis. Shaped articles of bone cement comprising active compounds can be implanted into soft tissue as local active compound depots having a delayed release of the active compounds.

For example, EP 0 202 445 A1 describes such a cytostatic-comprising bone cement and a drug depot with particularly favourable release properties produced therefrom. It can be seen from this specification that the particular active compound is admixed to the base material of the bone cement, that is to say the prepolymer and/or the monomer, as a finely divided powder, so that it is then present as a homogeneous distribution in the resulting polymer.

In practice, however, it has been found here that providing the bone cement components in a prefabricated form in which either one of the components, preferably the polymer, already comprises the pharmaceutical active compound or in which the active compound is packed separately for addition during mixing does not meet the requirements which must be imposed on a medical product intended for implantation into the body. With such a bone cement comprising active compounds or its components, it is in fact impossible to carry out the final sterilization which is necessary, and is problem-free with corresponding products comprising no active compounds, by customary methods, such as irradiation with $\gamma$ radiation or gassing with ethylene oxide. Many of the pharmaceutical active compounds in question here are sensitive to the action of $\gamma$ radiation or ethylene oxide. This also applies in particular to cytostatics, such as, for example, the active compound methotrexate which is preferably employed here. Sterile filtration of the liquid monomer components to which finely powdered active compound is added leads in the end to separation of the active compound, which is essentially insoluble in the monomer. Providing all these three bone cement components would accordingly require the availability of the pharmaceutical active compound from a sterile production line. Production of a pharmaceutical active compound under entirely sterile conditions is extremely expensive for obvious reasons.

There was therefore the object of developing a process with which bone cements comprising active compounds or their precursors and also their secondary products can be provided in a sterile form in a simple manner.

SUMMARY OF THE INVENTION

It has now been found that a bone cement which is composed of a polymeric solid component, a liquid monomer component and a solution of a pharmaceutical active compound in an organic solvent, the content of which does not exceed 50% by weight, based on the liquid component, shows practically no change in respect of processibility, hardening properties and mechanical strength. With this composition and procedure, it is possible to subject the solution of the active compound to sterile filtration before combining it with the monomer component or the solid component, so that all these three components of the bone cement can be provided in a sterile form in a simple manner.

The invention thus relates to a process for the preparation of bone cements comprising active compounds and bone replacement materials or implantable drug depots produced therefrom, the bone cement being composed of about 50 to 75% by weight of a solid component comprising a finely divided polymer of acrylic and/or methacrylic acid esters and if appropriate other additives, such as polymerization catalysts, X-ray contrast media, fillers and dyestuffs, and about 25 to 50% by weight of a liquid component comprising an acrylic and/or methacrylic acid ester monomer and if appropriate other additives, such as polymerization accelerators and stabilizers, which are mixed to form a liquid to semi-solid paste, brought into a desired shape, if appropriate, and then hardened, which is characterized in that the active compound is dissolved in an organic solvent, the content of which does not exceed 50% by weight, based on the liquid component, and this solution is mixed with the liquid component or the solid component.

DETAILED DESCRIPTION OF THE PREFERRED EMBODIMENTS

All the customary bone cements based on acrylate/methacrylate and the starting substances customary for these can be used in the process according to the invention. Bone cements of this type are commercially obtainable. The expert is familiar with their composition and the nature of their processing.

To prepare a bone cement comprising active compounds, it is proposed according to the invention first to dissolve the pharmaceutical active compound in an organic solvent and then to mix this active compound solution with the liquid monomer component or the finely divided polymeric solid component of the bone cement. The active compound solution can be sterilized by sterile filtration without problems, so that all the components of the bone cement comprising active compounds, that is to say including the active compound solution, can thus be sterilized, kept ready in sterile form and processed under sterile conditions to give the ready-to-use bone cement.

All the customary organic solvents are essentially suitable for providing the active compound solution. Those solvents in which on the one hand the intended pharmaceutical is readily soluble, so that a solution of the highest possible concentration can be prepared, and with which on the other hand the liquid monomer components are readily miscible to form a homogeneous phase are expediently chosen. The amount of solvent is chosen such that it does not exceed 50% by weight, based on the liquid monomer component. This ensures that when the components are mixed to form the ready-to-use bone cement, the processing properties, the hardening characteristics and the mechanical strength of the hardened bone cement do not change. An amount of solvent such that its content is 5 to 25% by weight, and in particular 10 to 15% by weight, based on the liquid component, is preferably chosen.

The amount of pharmaceutical active compound employed depends on its specific activity, the medical indication and the particular profile of requirements of the bone cement or of the bone replacement material or drug depot to be produced therefrom. As a general rule, a content of pharmaceutical active compound of 0.1 to 5% by weight, based on the total amount of bone cement, is adequate; in individual cases, in particular for the production of implantable drug depots, the active compound content can also be higher, for example up to 40% by weight.

All pharmaceutical active compounds which on the one hand are appropriate in bone cements, in bone replacement materials and in implantable drug depots from the point of view of their action profile and which on the other hand are sufficiently stable towards the constituents of bone cements and the temperatures which arise during hardening can be incorporated according to the invention in bone cements in this manner. Preferred possible active compounds are cytostatics, such as methotrexate, cisplatin, cyclophosphamide, fluorouracil, doxorubicin and the like, antibiotics, such as gentamicin, clindamycin, vancomycin, teicoplanin and the like, and furthermore antiseptics and bone growth-promoting substances. The process according to the invention is particularly suitable for the preparation of bone cements which comprise cytostatics and for which final sterilization is not possible by the process to date. It has proved particularly suitable and advantageous for the cytostatic methotrexate.

Surprisingly, it has been found here that the release properties of methotrexate-containing bone cement which has been prepared by the process according to the invention is considerably better than if methotrexate is merely admixed, as previously, in the form of a finely divided solid to the bone cement components. The release characteristics approximately correspond to those of a methotrexate-containing bone cement to which additives such as amino acids, in particular as described in EP 0 202 445 A1, with particularly finely divided particles have been added to improve the release of the active compound. Such additives can therefore be dispensed with in bone cements prepared by the process according to the invention, without having to accept losses in the release characteristics.

Solvents which have proved to be particularly for suitable for methotrexate are 2-pyrrolidone, N-methylpyrrolidone, dimethylsulphoxide (DMSO), tetrahydrofuran, dioxane, ethylene glycol, propanediol or combinations thereof. 2-Pyrrolidone, N-methylpyrrolidone and a mixture of DMSO and propanediol in a ratio of 1:1 are particularly preferred.

Methotrexate can be employed in the form of the disodium salt or also in the form of the free acid. The solubility of the active compound in the solvents mentioned is such that for the customary range of the amount used for methotrexate, that is to say 0.1 to 4% by weight, based on the total amount of bone cement, the amount of solvent can be chosen at, for example, one tenth of the amount of monomer without problems.

When the methotrexate solution is added to and mixed with the liquid monomer, the active compound precipitates out of the liquid mixture in the form of a finely disperse solid. It is assumed that the presence of the active compound in the bone cement in this finely disperse form is responsible for the improved release characteristics compared with customary admixing.

The release properties of the active compound can of course also be influenced and if appropriate improved further by the known and customary additives. Possible such additives are amino acids, such as arginine and hydroxyapatite or sodium bicarbonate, if possible in finely divided form with particle sizes below 100 µm. The initial concentration of the release of the active compound in particular can be regulated by such additives.

The solid component, which is usually in the form of a bead polymer of a methyl methacrylate/methyl acrylate copolymer with particle sizes of between 5 and 250 µm, comprises a polymerization catalyst, such as, for example, dibenzoyl peroxide. It can furthermore comprise X-ray contrast media, such as, for example, zirconium dioxide, dyestuffs for identification, such as, for example, chlorophyll, and fillers, and if appropriate other additives. Customary additives are, for example, calcium phosphates which have an osteoinductive or osteoconductive action, such as, in particular, hydroxy-apatite and tricalcium phosphate. The content of all these additives can vary within a relatively wide range and depends on the particular profile of requirements of the bone cement or of the corresponding secondary products. As a rule, it scarcely exceeds 30% by weight, based on the solid component. The liquid monomer component, methyl methacrylate, as a general rule comprises a polymerization accelerator, such as dimethyl-p-toluidine, and hydroquinone as a stabilizer in amounts customary for these. Dyestuffs and other expedient additives can furthermore be present. The solid component can be sterilized without problems using γ radiation or with ethylene oxide; the liquid component and the active compound solution can each be subjected to sterile filtration. Both components can be transferred separately and under sterile conditions to corresponding containers.

The bone cement comprising active compounds is expediently provided in the form of a set which is composed of separate packs of the three main components. Component (a) includes the solid component comprising a finely divided polymer of acrylic and/or methacrylic acid esters and if appropriate other additives, such as polymerization catalysts, X-ray contrast media, fillers and dyestuffs, the content of which is about 50 to 75% by weight of the bone cement. Component (b) includes the liquid component comprising an acrylic and/or methacrylic acid ester monomer and if appropriate other additives, such as polymerization accelerators and stabilizers, the content of which is about 25 to 50% by weight of the bone cement. Component (c) includes the solution of the active compound in an organic solvent, the content of which does not exceed 50% by weight, based on the liquid component.

The amounts of the components are preferably coordinated with one another such that the total contents of the three packs are combined with one another. The amounts are coordinated according to the envisaged intended use and according to whether a low-viscosity, a medium-viscosity or a high-viscosity cement is required. The solid component here has been subjected to final sterilization by means of radiation or ethylene oxide, and the liquid monomer component and the active compound solution have each been subjected to sterile filtration and transferred to a suitable packaging under sterile conditions.

It is expedient to complete this set with a device for mixing and/or application of the bone cement. Corresponding devices are known and customary. Corresponding devices preferably allow mixing of the bone cement in vacuo and combined application of the cement by means of a bone cement syringe.

The preparation of the ready-to-use bone cement comprising active compounds and its further processing are carried out in a manner completely analogous to that for bone cement systems to date, except that the active compound solution and the liquid monomer component are first brought together and mixed with one another, and only then is the polymer powder added to this mixture. Similarly, it is also possible first to mix the polymer powder with the active compound solution and then to add the monomer. After intimate thorough mixing of the components, the polymerization starts due to the catalyst contained therein; the composition remains liquid to plastically deformable for some minutes; thereafter, the hardened end product has formed.

The bone cement comprising active compounds can be used in the customary manner during the liquid or plastic stage for implantation of bone prostheses. The surgeon can also process the composition to shaped articles of any desired shape and size and, after hardening, implant these as local active compound depots into the body regions to be treated. Such implantable drug depots can also already be provided in prefabricated form.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application German Patent No. P 44 33 201.7, are hereby incorporated by reference.

EXAMPLE 25 g of methotrexate acid are dissolved in 1 liter of 2-pyrrolidone, the solution is subjected to sterile filtration over a 0.2 μm Teflon filter and transferred to in each case brown 1 ml injection bottles under sterile conditions, and the bottles are closed.

The methotrexate solution is removed from the bottle with a sterile syringe and mixed with 10 ml of methyl methacrylate. Methotrexate thereby precipitates in finely disperse form.

Bone cement powder having the composition of 15.5 g of PMMA/PMA copolymer (94/6), 3 g of hydroxy-apatite powder (2–5 μm) and 2 g of zirconium dioxide powder is added to the suspension.

The monomer and polymer comprise the customary starter system of dimethyl-para-toluidine and dibenzoyl peroxide.

After thorough mixing, the cement is ready to use.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the formation of bone cements or replacements comprising an active compound selected from the group consisting of cytostatics, antibiotics, antiseptics and bone growth-promoting substances and additionally comprising a) about 50 to 75% by weight of a solid component comprising a finely divided polymer of acrylic acid esters, methacrylic acid esters or both and optionally additives, and b) about 25 to 50% by weight of a liquid component comprising an acrylic acid ester monomer, methacrylic acid ester monomer or both and optionally additives, wherein weight percents are based on the total weight of a+b, said process comprising mixing the solid component and liquid component to form a liquid to semi-solid paste, optionally bringing the mixture into a desired shape and optionally hardening the mixture, wherein the active compound is dissolved in an organic solvent selected from the group consisting of 2-pyrrolidone, N-methylpyrrolidone, dimethylsulfoxide, tetrahydrofuran, dioxane, ethylene glycol, propanediol or combinations thereof, and the amount of said organic solvent does not exceed 50% by weight, based on the liquid component (b), and wherein the active compound dissolved in an organic solvent is mixed with the liquid component or the solid component and the solid component is subjected to final sterilization prior to mixing the solid component and liquid component to form a liquid to semi-solid paste by means of radiation, ethylene oxide or both and the liquid component and organic solvent are subjected to sterile filtration.

2. A process according to claim 1, characterized in that the amount of solvent is 5 to 25% by weight, based on the liquid component.

3. A process according to claim 1, characterized in that methotrexate is used as the active compound.

4. A process as in claim 1 comprising the additional step of forming the mixture into a desire shape and hardening the mixture.

5. A process as in claim 1, wherein the optional additives for the solid component comprise catalysts, x-ray contrast media, fillers and dye-stuffs.

6. A process as in claim 1, wherein the optional additives for the liquid component comprise polymerization accelerators and stabilizers.

* * * * *